(12) United States Patent
Ashby

(10) Patent No.: US 12,262,895 B2
(45) Date of Patent: Apr. 1, 2025

(54) OCCLUSIVE DEVICES WITH SPIRAL STRUTS FOR TREATING VASCULAR DEFECTS

(71) Applicant: Covidien LP, Mansfield, MA (US)

(72) Inventor: Mark Philip Ashby, Laguna Niguel, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/649,920

(22) Filed: Feb. 3, 2022

(65) Prior Publication Data
US 2023/0240686 A1    Aug. 3, 2023

(51) Int. Cl.
*A61B 17/12* (2006.01)

(52) U.S. Cl.
CPC .. *A61B 17/12118* (2013.01); *A61B 17/12145* (2013.01); *A61B 2017/12054* (2013.01)

(58) Field of Classification Search
CPC ........ A61B 17/12022; A61B 17/12113; A61B 17/12109; A61B 17/12031; A61B 17/12036; A61B 17/1204; A61B 17/1214; A61B 17/1215; A61B 17/12145; A61B 17/12154; A61B 17/12118; A61B 2017/12054
See application file for complete search history.

(56) References Cited

U.S. PATENT DOCUMENTS

| | | | | |
|---|---|---|---|---|
| 6,231,561 B1 * | 5/2001 | Frazier | ............... | A61B 17/0401 604/500 |
| 2003/0181942 A1 * | 9/2003 | Sutton | ............... | A61B 17/0057 606/200 |
| 2012/0071911 A1 * | 3/2012 | Sadasivan | ........ | A61B 17/12145 606/191 |
| 2013/0116774 A1 | 5/2013 | Strauss et al. | | |
| 2014/0135812 A1 * | 5/2014 | Divino | ............. | A61B 17/12118 623/1.11 |
| 2016/0120551 A1 | 5/2016 | Connor | | |
| 2016/0331382 A1 * | 11/2016 | Center | ............. | A61B 17/12177 |
| 2017/0367707 A1 * | 12/2017 | Divino | ................... | A61F 2/966 |
| 2018/0140305 A1 | 5/2018 | Connor | | |
| 2020/0155333 A1 | 5/2020 | Franano et al. | | |
| 2021/0085333 A1 | 3/2021 | Gorochow et al. | | |

FOREIGN PATENT DOCUMENTS

| | | |
|---|---|---|
| EP | 1076518 B1 | 12/2005 |
| WO | 2020139544 A2 | 7/2020 |

* cited by examiner

*Primary Examiner* — Phong Son H Dang
(74) *Attorney, Agent, or Firm* — Fortem IP LLP

(57) ABSTRACT

Devices for treating vascular defects and associated systems and methods are disclosed herein. In some embodiments, for example, an occlusive device for treating an aneurysm includes a tubular structure having a first end portion with a first opening, a second end portion with a second opening, and a mesh surface extending between the first and second end portions. The occlusive device also includes a plurality of spiral struts coupled to the first end portion of the tubular structure and extending over the first opening. When the occlusive device is deployed within the aneurysm, the tubular structure and the plurality of spiral struts can be configured to self-expand such that the plurality of spiral struts span a neck of the aneurysm substantially within a single plane and the mesh surface of the tubular structure engages a wall of the aneurysm near the neck.

27 Claims, 9 Drawing Sheets

OCCLUSIVE DEVICES WITH SPIRAL STRUTS FOR TREATING VASCULAR DEFECTS

TECHNICAL FIELD

The present technology generally relates to medical devices, and in particular, to occlusive devices for treating vascular defects.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Endovascular treatment of intracranial aneurysms with coil embolization involves packing the aneurysm sac with metal coils to reduce or disrupt the flow of blood into the aneurysm, thereby enabling a local thrombus or clot to form which fills and ultimately closes off the aneurysm. Although coiling has proven to have better outcomes than surgical clipping for both ruptured and unruptured aneurysms, treating complex aneurysms using conventional coiling is challenging. This is especially true for wide-necked aneurysms because coil segments may protrude from the aneurysm sac through the neck of the aneurysm and into the parent vessel, causing serious complications for the patient.

To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-necked aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual antiplatelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

The above-noted drawbacks associated with balloon- and stent-assisted coiling techniques influenced the development of intraluminal flow diverting stents, or stent-like structures implanted in the parent vessel across the neck of the aneurysm that redirect blood flow away from the aneurysm, thereby promoting aneurysm thrombosis. Flow diverters have been successfully used for treating wide-necked, giant, fusiform, and blister-like aneurysms. However, because they are positioned in the parent vessel, flow diverters require DAPT to avoid clot formation on the stent itself and ischemic complications. This, in turn, increases the risk and severity of hemorrhagic complications in patients with acutely ruptured aneurysms or other hemorrhagic risks. Thus, flow diverters are not indicated for the treatment of ruptured aneurysms. Flow diverters have also shown limited efficacy in treating bifurcation aneurysms (35-50%).

Endosaccular flow disrupting devices have the potential to provide the intra-aneurysmal flow disruption of coiling with the definitive remodeling at the aneurysm-parent vessel interface achieved by intraluminal flow diverters. Endosaccular devices can be mesh devices configured to be deployed completely within the aneurysm sac, with the interstices of the mesh covering the aneurysm neck and reconstructing the aneurysm-parent vessel interface. The implant disrupts the blood flow entering and exiting the aneurysm sac (resulting in stasis and thrombosis) and supports neoendothelial overgrowth without requiring DAPT (unlike endoluminal flow diverters). Thus, endosaccular devices can be used to treat wide-necked aneurysms and ruptured aneurysms. Moreover, because the device is placed completely within the aneurysm sac, the parent and branch vessels are unimpeded and can be accessed for any further retreatment or subsequent deployment of adjunctive devices during treatment.

Accordingly, there is a need for improved devices, systems, and methods for treating aneurysms and other vascular defects.

SUMMARY

The subject technology is illustrated, for example, according to various aspects described below. These are provided as examples and do not limit the subject technology.

In one aspect of the present technology, an occlusive device for treating an aneurysm is provided. The occlusive device can include a tubular structure having a first end portion with a first opening, a second end portion with a second opening, and a mesh surface extending between the first and second end portions. The occlusive device can also include a plurality of spiral struts coupled to the first end portion of the tubular structure and extending over the first opening. When the occlusive device is deployed within the aneurysm, the tubular structure and the plurality of spiral struts can be configured to self-expand such that the plurality of spiral struts span a neck of the aneurysm substantially within a single plane and the mesh surface of the tubular structure engages a wall of the aneurysm near the neck.

In some embodiments, the tubular structure includes a stent including a plurality of cells.

In some embodiments, the tubular structure includes a braid formed from a plurality of filaments. The plurality of spiral struts can be formed from the plurality of filaments.

In some embodiments, the plurality of spiral struts are arranged in a radial configuration.

In some embodiments, the occlusive device further includes a hub. Each spiral strut can include a first end region coupled to the hub, and a second end region coupled to the first end portion of the tubular structure. The second end region of each spiral strut can be coupled to a peripheral edge of the tubular structure. The second end regions of the plurality of spiral struts can be spaced apart along the peripheral edge of the tubular structure.

In some embodiments, the occlusive device further includes a detachment element configured to releasably couple the tubular structure and the plurality of spiral struts to a pusher member. The occlusive device can further include a hub. The detachment element can be coupled to the plurality of spiral struts via the hub. Optionally, the occlusive device includes an elongate member connecting the detachment element to the hub. The elongate member can be configured to transform from a first state to a second state when the occlusive device is deployed within the aneurysm. When in the first state, the elongate member can extend away from the tubular structure. When in the second state, the elongate member can be positioned at least partially within the tubular structure.

In some embodiments, when the occlusive device is deployed within the aneurysm, the plurality of spiral struts are contained entirely within the aneurysm. When the occlusive device is deployed within the aneurysm, the plurality of spiral struts can be configured to exert outwardly directed forces to enhance the engagement between the mesh surface and the wall of the aneurysm.

In some embodiments, the tubular structure is integrally formed with the plurality of spiral struts as a single unitary component.

In some embodiments, the tubular structure and the plurality of spiral struts are discrete components that are attached to each other.

In another aspect of the present technology, an occlusive device for treating an aneurysm is provided. The occlusive device can include a tubular structure having a first end portion and a second end portion opposite the first end portion. The occlusive device can also include a plurality of curved struts coupled to the first end portion of the tubular structure, each curved strut including a first end region and a second end region. The occlusive device can further include a hub. The plurality of curved struts can be arranged in a spiral configuration with the first end region of each curved strut coupled to the hub, and the second end region of each curved strut coupled to the first end portion of the tubular structure.

In some embodiments, the tubular structure includes a stent.

In some embodiments, the tubular structure includes a braid.

In some embodiments, the second end region of each curved strut is coupled to a peripheral edge of the tubular structure. The second end region of each curved strut can be spaced apart along the peripheral edge of the tubular structure.

In some embodiments, the first end portion of the tubular structure includes a first opening, and the plurality of curved struts are disposed over the first opening.

In some embodiments, the occlusive device further includes a detachment element configured to releasably couple the tubular structure and the plurality of curved struts to a pusher member. The detachment element can be coupled to the plurality of curved struts via the hub.

In some embodiments, the occlusive device further includes an elongate member connecting the detachment element to the hub. The elongate member can be configured to transform from a first state to a second state when the occlusive device is deployed within the aneurysm.

In some embodiments, the tubular structure and plurality of curved struts are configured to self-expand when deployed within the aneurysm. When deployed within the aneurysm, the plurality of curved struts can be disposed across a neck of the aneurysm and the tubular structure engages a wall of aneurysm near the neck. When deployed within the aneurysm, the plurality of curved struts can lie substantially within a single plane. When deployed within the aneurysm, the plurality of curved struts can be configured to exert outwardly directed forces to enhance the engagement between the tubular structure and the wall of the aneurysm.

In some embodiments, the tubular structure is integrally formed with the plurality of curved struts as a single unitary component.

In some embodiments, the tubular structure and the plurality of curved struts are discrete components that are attached to each other.

In a further aspect of the present technology, a method of treating an aneurysm is provided. The method can include introducing an occlusive device at least partially into the aneurysm. The occlusive device can include a tubular structure coupled to a plurality of spiral struts, the tubular structure having a mesh outer surface. The method can also include expanding the occlusive device such that the plurality of spiral struts extend across a neck of the aneurysm and the mesh outer surface of the tubular structure engages a wall of the aneurysm near the neck.

In some embodiments, the occlusive device is introduced to the aneurysm via a first elongate shaft. The occlusive device can be disposed within the first elongate shaft in a low-profile configuration. Expanding the occlusive device can include advancing the occlusive device out of the first elongate shaft such that the occlusive device self-expands into an expanded configuration. The plurality of spiral struts can be coupled to a proximal end portion of the tubular structure. When the occlusive device is in the low-profile configuration, the plurality of spiral struts can extend proximally from the proximal end portion of the tubular structure by at least a first distance. When the occlusive device is in the expanded configuration, the plurality of spiral struts can extend proximally from the proximal end portion of the tubular structure by no more than a second distance, the second distance being smaller than the first distance. When the occlusive device is in the expanded configuration, the plurality of spiral struts can lie substantially within a single plane. When the occlusive device is in the expanded configuration, the plurality of spiral struts can conform to a diameter of the neck of the aneurysm.

In some embodiments, the method further includes introducing the first elongate shaft into the aneurysm, and delivering an embolization element into the aneurysm via the first elongate shaft. Introducing the first elongate shaft into the aneurysm can include positioning a distal tip portion of the first elongate shaft between the plurality of spiral struts. The method can further include retaining the embolization element within the aneurysm via the occlusive device.

In some embodiments, the tubular structure includes a stent.

In some embodiments, the tubular structure includes a braid.

In some embodiments, the method further includes releasing the occlusive device from a pusher member. The occlusive device can be coupled to the pusher member via a hub. Each spiral strut can include a first end region coupled to the hub, and a second end region coupled to the tubular structure. Optionally, the hub includes a detachment element configured to releasably couple to the pusher member.

In some embodiments, the method further includes introducing a second elongate shaft into the aneurysm, and delivering an embolization element into the aneurysm via the second elongate shaft. Introducing the second elongate shaft can include positioning a distal tip portion of the second elongate shaft between the plurality of spiral struts. The method can also include retaining the embolization element within the aneurysm via the occlusive device.

Additional features and advantages of the present technology will be set forth in the description below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
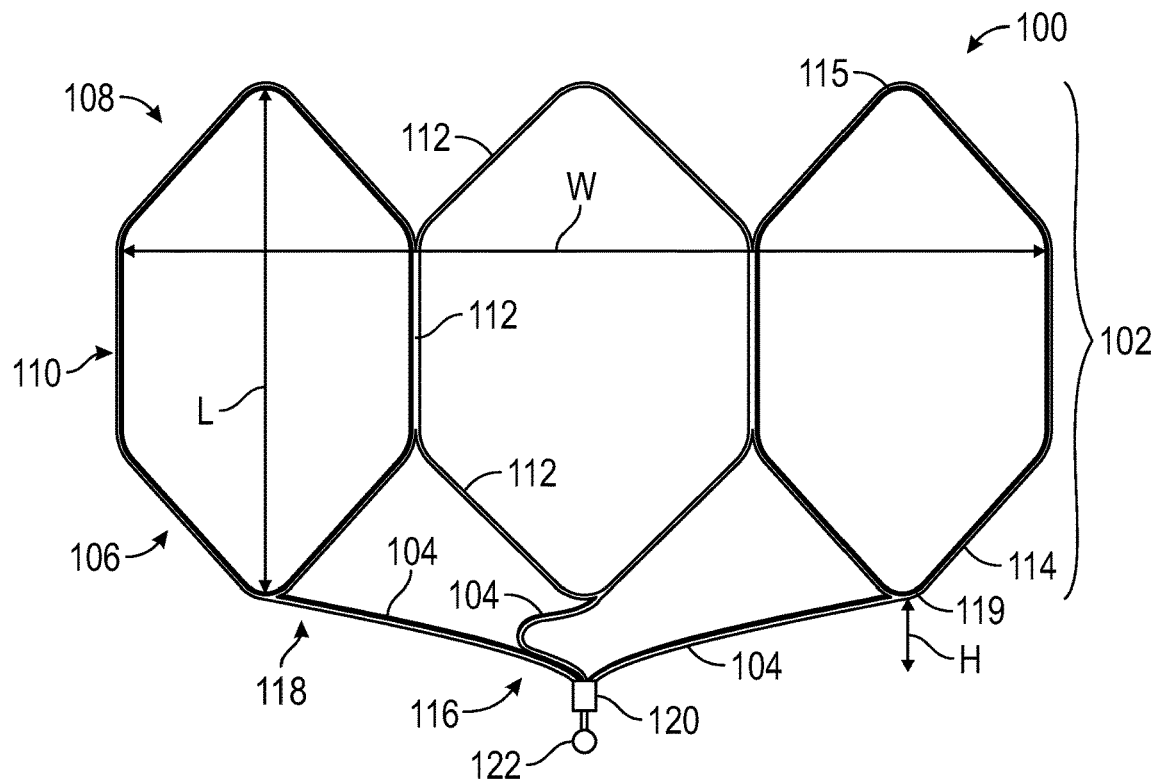
FIG. 1A is a side view of an occlusive device in an expanded configuration, in accordance with embodiments of the present technology.

The present technology relates to devices for treating vascular defects such as aneurysms, and associated systems and methods. In some embodiments, for example, an occlusive device for treating an aneurysm includes a tubular structure (e.g., a tubular stent or braid) having a first end portion with a first opening, a second end portion with a second opening, and a mesh surface extending between the first and second end portions. The occlusive device can also include a plurality of spiral struts coupled to the first end portion of the tubular structure and extending over the first opening. When the occlusive device is deployed within the aneurysm, the tubular structure and the plurality of spiral struts can self-expand such that the plurality of spiral struts span a neck of the aneurysm and the mesh surface of the tubular structure engages a wall of the aneurysm near the neck.

The occlusive devices of the present technology can provide many advantages compared to conventional device for treating an aneurysm. For example, the use of spiral struts enables the occlusive device to expand outward to conform to different neck geometries, while keeping the struts substantially in-plane with the aneurysm neck and/or out of the parent vessel. Accordingly, the occlusive devices disclosed herein can be used to treat a wider range of aneurysm sizes (e.g., aneurysms having a neck diameter from 3 mm to 5 mm) and/or shapes (e.g., aneurysm necks having a non-circular shape, such as oblong or peanut-shaped), as well as challenging aneurysm types such as wide-necked aneurysms (e.g., aneurysms having a neck diameter greater than 4 mm and/or a dome-to-neck ratio less than 2). Additionally, the spiral struts can brace the tubular structure radially outward against the wall of the aneurysm near the neck, thus reducing the likelihood of the device becoming dislodged and/or prolapsing into the parent vessel. Once deployed, the devices herein can be contained partially or entirely within the aneurysm sac with little or no protrusion into the parent vessel, thus reducing the likelihood of clot formation and/or avoiding the need for concomitant DAPT.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

As used herein, the terms "vertical," "lateral," "upper," and "lower" can refer to relative directions or positions of features of the embodiments disclosed herein in view of the orientation shown in the Figures. For example, "upper" or "uppermost" can refer to a feature positioned closer to the top of a page than another feature. These terms, however, should be construed broadly to include embodiments having other orientations, such as inverted or inclined orientations where top/bottom, over/under, above/below, up/down, and left/right can be interchanged depending on the orientation.

Figure 1B:
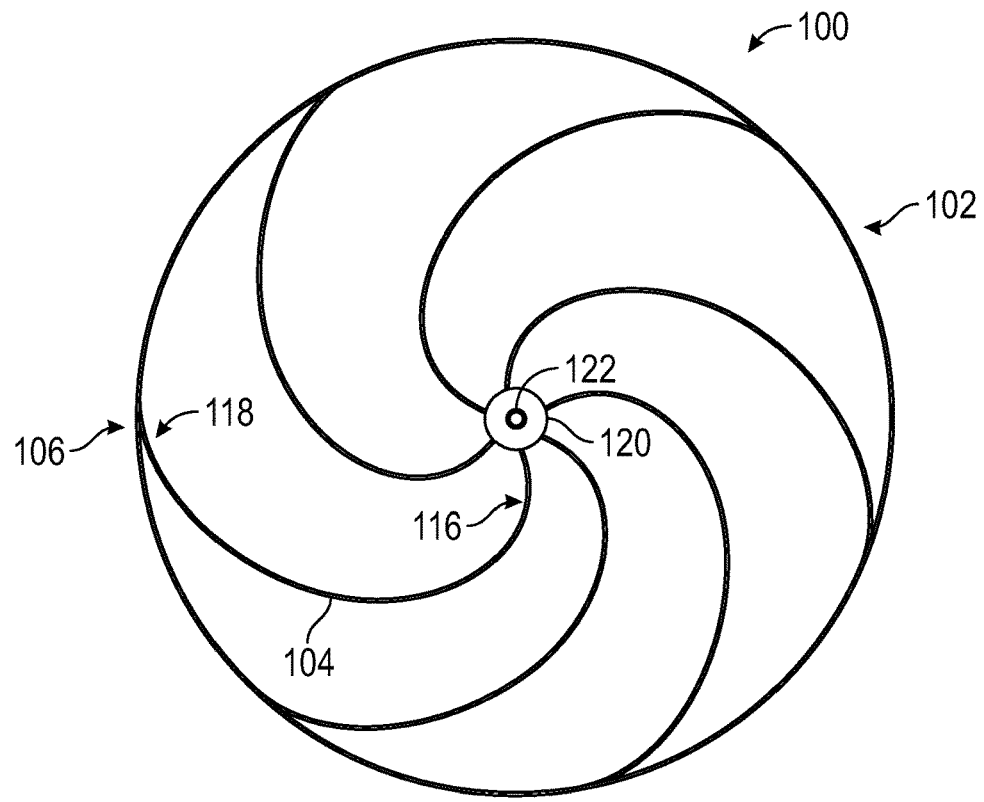
FIG. 1B is a bottom view of the occlusive device of FIG. 1A.

FIGS. 1A and 1B are perspective and bottom views, respectively, of an occlusive device 100 ("device 100") for treating an aneurysm, in accordance with embodiments of the present technology. Referring first to FIG. 1A, the device 100 is configured to be deployed within an aneurysm sac. As described further below, the device 100 can be positioned over the neck of the aneurysm to prevent an embolization element (e.g., a coil) from prolapsing from the aneurysm sac into the parent vessel. The device 100 can also reduce or prevent blood flow from the parent vessel into the aneurysm sac, and/or provide a scaffold for endothelial cell attachment. The growth and development of an endothelial layer over the aneurysm neck can wall off the aneurysm from the parent vessel and allow flow dynamics to equilibrate at the defect. Upon endothelialization, the fluid pressure can be evenly distributed along the parent vessel in a manner that prevents recanalization at the defect post-treatment. Moreover, blood from within the parent vessel no longer has access to the walled-off defect once the endothelialization process is complete. Accordingly, the device 100 can facilitate healing of the defect and/or prevent recanalization.

The device 100 includes a tubular structure 102 coupled to a plurality of curved struts 104. The tubular structure 102 is configured to anchor the device 100 at or near the neck of the aneurysm, while the curved struts 104 are configured to retain an embolization element within the device 100, as described in further detail below. The tubular structure 102 includes a proximal end portion 106, a distal end portion 108, and a mesh surface 110 extending between the proximal end portion 106 and distal end portion 108. In some embodiments, the proximal end portion 106 and distal end portion 108 each have a respective opening, such that the tubular structure 102 includes a lumen extending between the proximal end portion 106 and distal end portion 108, and surrounded by the mesh surface 110. The length L of the tubular structure 102 (e.g., as measured from the proximal end portion 106 to the distal end portion 108 when the device 100 is fully expanded) can be no more than 4 mm, 3.5 mm, 3 mm, 2.5 mm, 2 mm, 1.5 mm, or 1 mm. The width W or diameter of the tubular structure 102 (e.g., as measured when the device 100 is fully expanded) can be at least 5 mm, 4.5 mm, 4 mm, 3.5 mm, 3 mm, 2.5 mm, 2 mm, 1.5 mm, or 1 mm. Although FIG. 1B depicts the tubular structure 102 as having a circular cross-sectional shape, in other embodiments, the tubular structure 102 can have a different shape (e.g., oval, triangular, square, pentagonal, hexagonal, heptagonal, octagonal).

In the embodiment of FIGS. 1A and 1B, the tubular structure 102 is a stent or stent-type structure, with the mesh surface 110 including a plurality of elongate members 112 (e.g., struts) that are interconnected to form cells 114. The geometry of the cells 114 and elongate members 112 can be configured in many different ways. In the illustrated embodiment, for example, the cells 114 are six-sided (e.g., hexagonal) closed cells. The distal apices 115 of the cells 114 can be rounded to reduce the likelihood of tissue perforation when deploying the device 100 in the aneurysm. In other embodiments, however, some or all of the cells 114 can have a different number of sides (e.g., three, four, five, or more), shape (e.g., triangular, square, rectangular, diamond, trapezoidal, parallelogram, pentagonal), be open rather than closed, have sharp distal apices 115 rather than rounded distal apices 115, and/or any other suitable configuration. Additionally, although the tubular structure 102 in FIG. 1A includes a single circumferential ring of cells 114, in other embodiments, the tubular structure 102 can include multiple circumferential rings of cells 114 arranged longitudinally between the proximal end portion 106 and the distal end portion 108. Moreover, although the elongate members 112 are shown as being linear, in other embodiments, some or all of the elongate members 112 can be curved (e.g., sinusoidal, serpentine), curvilinear, or any other suitable geometry. The size (e.g., length, width, height, perimeter, cell area) of the cells 114 can also be varied as desired.

The curved struts 104 are connected to the proximal end portion 106 of the tubular structure 102. As best seen in FIG. 1B, the curved struts 104 are disposed over the opening of the proximal end portion 106 of the tubular structure 102 in a spiral and/or helical configuration. Accordingly, the curved struts 104 may also be referred to interchangeably herein as "spiral struts" or "helical struts." The curvature of the curved struts 104 can be oriented in the same direction, such as in a clockwise direction or a counterclockwise direction, to form the spiral and/or helical configuration.

In some embodiments, each curved strut 104 includes a first end region 116 (e.g., a proximal end region) coupled to a hub 120 and a second end region 118 (e.g., a distal end region) coupled to the proximal end portion 106 of the tubular structure 102. The second end region 118 of each curved strut 104 can be coupled to a proximal apex 119 of a respective cell 114 of the tubular structure 102. In other embodiments, however, the second end region 118 can be coupled to a different portion of the cell 114, such as to a lateral edge of the cell 114. The hub 120 can be generally aligned with the center of the opening of the proximal end portion 106, and the second end regions 118 of the curved struts 104 can be spaced apart along the peripheral edge of the proximal end portion 106, such the separation distance between the curved struts 104 increases as the curved struts 104 radiate outward from the hub 120. The spacing between the curved struts 104 can be sufficiently large to permit an embolization element delivery device (e.g., a microcatheter or other elongate shaft) to pass through, but sufficiently small such that the embolization element does not prolapse into the parent vessel. In some embodiments, the average and/or maximum distance between neighboring curved struts 104 is no more than 2.5 mm, 2.25 mm, 2 mm, 1.75 mm, 1.5 mm, 1.25 mm, 1 mm, 0.75 mm, or 0.5 mm.

The configuration of the curved struts 104 can be varied in many different ways.

For example, although FIG. 1B depicts the device 100 as including six curved struts 104, in other embodiments, the device 100 can include a different number of curved struts 104 (e.g., two, three, four, five, seven, eight, nine, ten, 20, or more). As another example, although each curved strut 104 is shown as having the same geometry (e.g., length, width, thickness, curvature), in other embodiments, some or all of the curved struts 104 can have different geometries. In a further example, although FIG. 1B depicts the curved struts 104 as being evenly spaced, in other embodiments the spacing can be varied as desired (e.g., the struts 104 can be clustered into one or more groups that are separated by larger gaps).

Referring to FIGS. 1A and 1B together, when the device 100 is deployed within the aneurysm, the tubular structure 102 is configured to self-expand such that the mesh surface 110 engages the inner wall of the aneurysm sac and applies a radially outward bracing force to anchor the device 100 at the desired location. The curved struts 104 also self-expand together with the tubular structure 102 to bridge the aneurysm neck. Optionally, the expansion of the curved struts 104 can also exert forces in a radially outward direction to further enhance engagement of the tubular structure 102 with the aneurysm wall. In yet another option, the expansion of the curved struts 104 is at least partially caused by the expansion of the tubular structure 102. In some embodiments, the spiral and/or helical configuration of the curved struts 104 enables the curved struts 104 to expand to a wider range of neck diameters while lying substantially within a single plane. Stated differently, the height H (FIG. 1A) of each curved strut 104 in its expanded configuration (e.g., as measured vertically from the first end region 116 to the second end region 118) can be no more than 25%, 20%, 15%, 10%, 5%, 2%, 1%, or 0.1% of the width W of the tubular structure 102. For example, the height H in the expanded configuration can be no more than 1.25 mm, 1 mm, 0.5 mm, 0.25 mm, or 0.1 mm. Accordingly, when deployed, the curved struts 104 can be contained partially or entirely within the aneurysm sac with little or no protrusion into the parent vessel, even if the device 100 is not fully expanded to its maximum diameter. In contrast, other strut designs (e.g., straight struts) may not be substantially planar if the device is not fully expanded, and thus may extend significantly out of the aneurysm and into the parent vessel after deployment.

In the illustrated embodiment, the hub 120 is a collar, band, ring, etc., that crimps or otherwise holds the first end regions 116 of the curved struts 104 together. Alternatively, the hub 120 can simply be the location where the first end regions 116 are connected to each other (e.g., via welding, bonding, adhesives), rather than a separate component. As best seen in FIG. 1A, the hub 120 can be coupled to a detachment element 122 configured to releasably couple to a pusher member (not shown). The pusher member can be an elongate rod, shaft, wire, etc., that is configured to push the device 100 through a distal end of a delivery catheter to deploy the device 100 within the aneurysm, as described further below. Optionally, the pusher member can also be used to pull the device 100 partially or fully back into the delivery catheter, e.g., for repositioning purposes. The detachment element 122 can utilize any suitable detachment technique known to those of skill in the art, such as electrolytic detachment, mechanical detachment, thermal detachment, electromagnetic detachment, or combinations thereof. An example of a detachment element for suitable use with the present technology is the Axium™ or Axium™ Prime Detachable Coil System (Medtronic).

Optionally, the device 100 can include one or more radiopaque portions so the physician can visualize the location and configuration of the device 100 during deployment in the aneurysm. For example, radiopaque markers (not shown) can be incorporated into the device 100 at or near the distal apices 115, at or near the proximal apices 119, at or near the intersections of adjacent cells 114, at or near the second end regions 118 of the curved struts 104, at or near the first end regions 116 of the curved struts 104, and/or on or within the hub 120.

The device 100 can be manufactured in many different ways. For example, the tubular structure 102 and/or curved struts 104 can be formed by laser-cutting of a tube or sheet, etching, metal injection molding, braiding, or any other suitable manufacturing process. In some embodiments, the tubular structure 102 and curved struts 104 are integrally formed as a single unitary component. In other embodiments, the tubular structure 102 and curved struts 104 can be discrete components that are attached to each other, e.g., using welding, adhesives, fasteners, or other suitable techniques. The tubular structure 102 and/or curved struts 104 can be formed of known flexible materials, including shape memory and/or superelastic materials (e.g., Nitinol), cobalt chromium, platinum, stainless steel, other metals or metal alloys, or a combination thereof. Optionally, portions of the tubular structure 102 and/or curved struts 104, or the entirety of the tubular structure 102 and/or curved struts 104, can include one or more coatings or surface treatments, such as coatings or treatments to increase lubricity and/or reduce the delivery force as the device 100 is advanced through the delivery catheter, increase hydrophilicity, and/or enhance blood compatibility and reduce thrombogenic surface activity. For example, an anti-thrombogenic coating or treatment can be applied to the curved struts 104, hub 120, and/or detachment element 122.

In some embodiments, the device 100 is configured to transform between a first, low-profile configuration suitable for delivery via an elongate shaft (e.g., a delivery catheter) and a second, expanded configuration suitable for bridging the neck of an aneurysm (e.g., the configuration illustrated in FIGS. 1A and 1B). In such embodiments, the tubular structure 102 and/or curved struts 104 can be shape set (e.g., heat set) in the expanded configuration, such that the device 100 self-expands into the expanded configuration when deployed into the aneurysm. For example, the tubular structure 102 and curved struts 104 can both be shape set into a fully expanded configuration in which the tubular structure 102 is opened to its maximum width and/or diameter, and/or the distance spanned by the curved struts 104 is substantially equal to the maximum width and/or diameter of the tubular structure 102. In such embodiments, the self-expansion of the curved struts 104 can actively push the tubular structure 102 radially outward to further enhance engagement with the aneurysm wall. Alternatively, the tubular structure 102 can be shape set in the fully expanded configuration, while the curved struts 104 are shape set into a partially expanded configuration in which the distance spanned by the curved struts 104 is less than the maximum width and/or diameter of the tubular structure 102. In such embodiments, the curved struts 104 can be "passive" elements that are pulled open by the self-expansion of the tubular structure 102.

FIGS. 2A-2G illustrate a method of treating an aneurysm with an occlusive device, in accordance with embodiments of the present technology. Although the illustrated embodiment is shown and described in terms of the device 100 of FIGS. 1A and 1B, the method can be applied to any embodiment of the occlusive devices described herein (e.g., the devices 300, 400 of FIGS. 3A-4B).

Figure 2A:
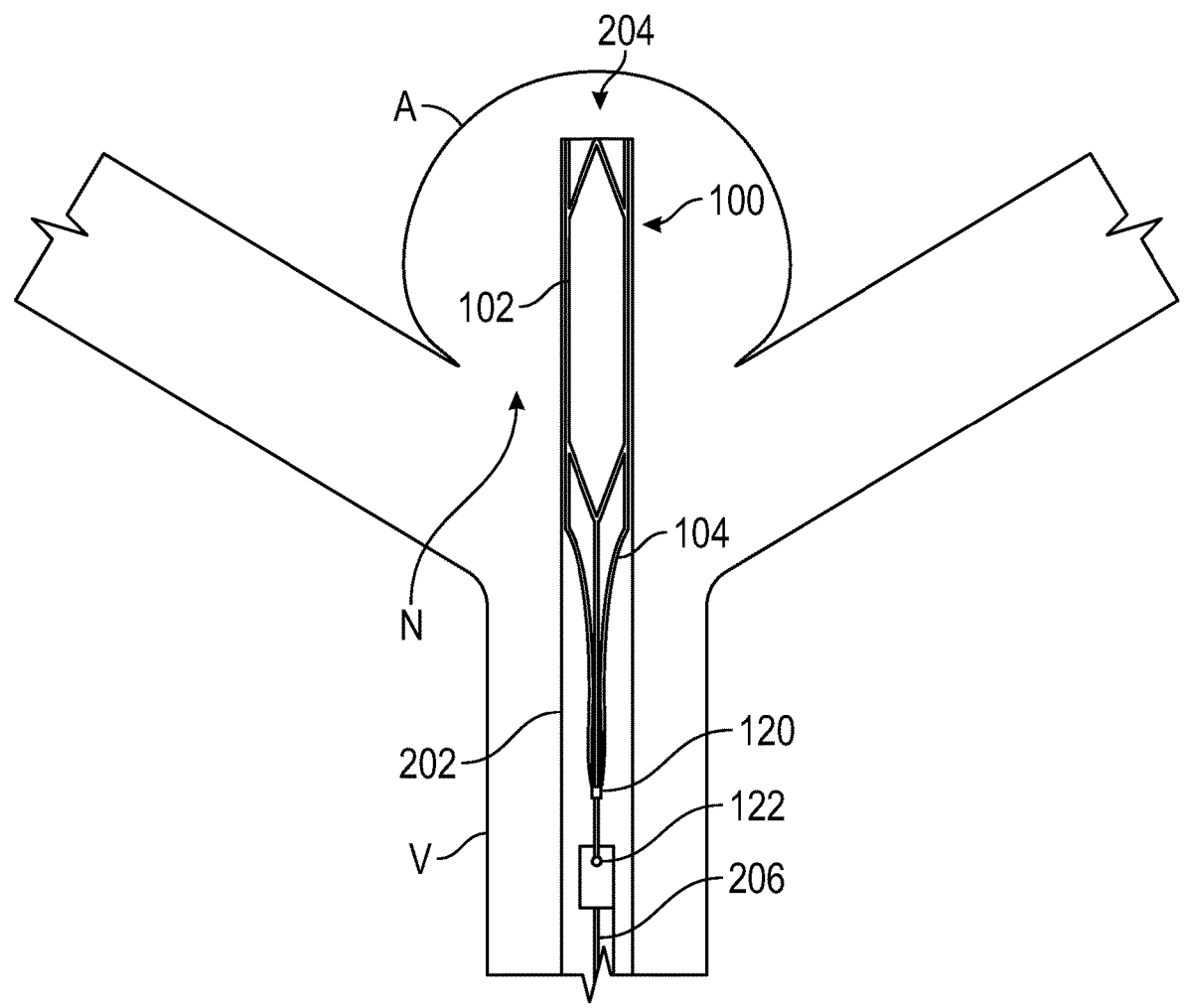
FIG. 2A is a partially schematic side view of an occlusive device being introduced into an aneurysm, in accordance with embodiments of the present technology.

Referring first to FIG. 2A, the device 100 can be loaded within a first elongate shaft 202 (e.g., a delivery catheter such as a microcatheter) in a low-profile configuration. When in the low-profile configuration, the tubular structure 102 and curved struts 104 of the device 100 can be compressed, flattened, or otherwise compacted in a generally linear configuration to conform to the interior lumen of the first elongate shaft 202. In the illustrated embodiment, for example, the curved struts 104 are constrained in a generally straightened state and extend proximally away from the tubular structure 102. The distance between the most proximal portion of the curved struts 104 and the most proximal portion of the tubular structure 102 can be at least 1 mm, 2 mm, 3 mm, 4 mm, or 5 mm. The device 100 can then be intravascularly delivered to a location within a blood vessel V adjacent a target aneurysm A via the first elongate shaft 202. As shown in FIG. 2A, a distal tip 204 of the first elongate shaft 202 can be advanced through the neck N of the aneurysm A and into an interior cavity of the aneurysm A.

Figure 2B:
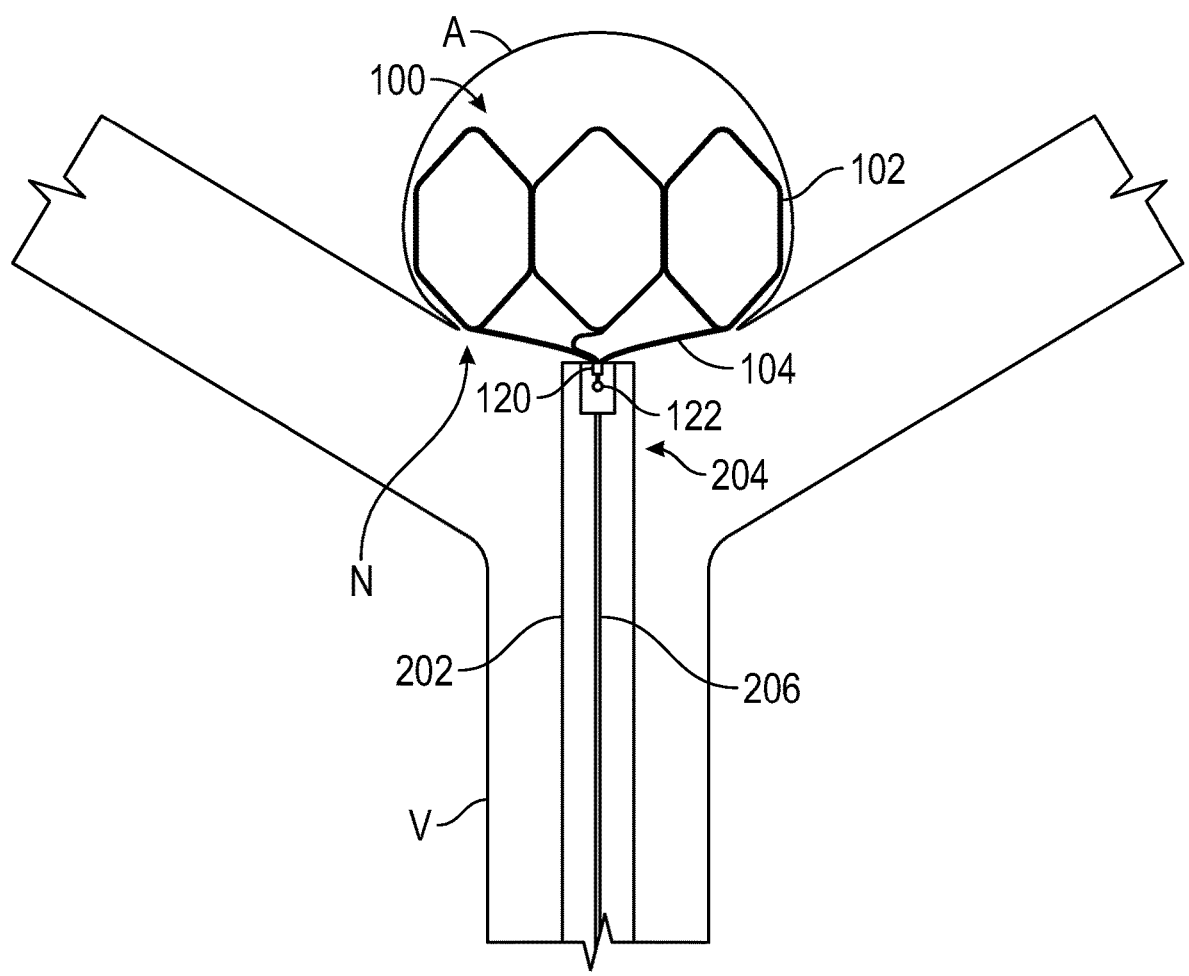
FIG. 2B is a partially schematic side view of the occlusive device of FIG. 2A being deployed in the aneurysm.

Referring next to FIG. 2B, the device 100 can then be deployed by pushing the device 100 distally through the opening in the distal tip 204 of the first elongate shaft 202 and into the aneurysm cavity, e.g., using a pusher member 206 coupled to the detachment element 122 and/or hub 120. As the tubular structure 102 and curved struts 104 of the device 100 exit the first elongate shaft 202, these components can self-expand from the low-profile configuration into the expanded configuration.

Figure 2C:
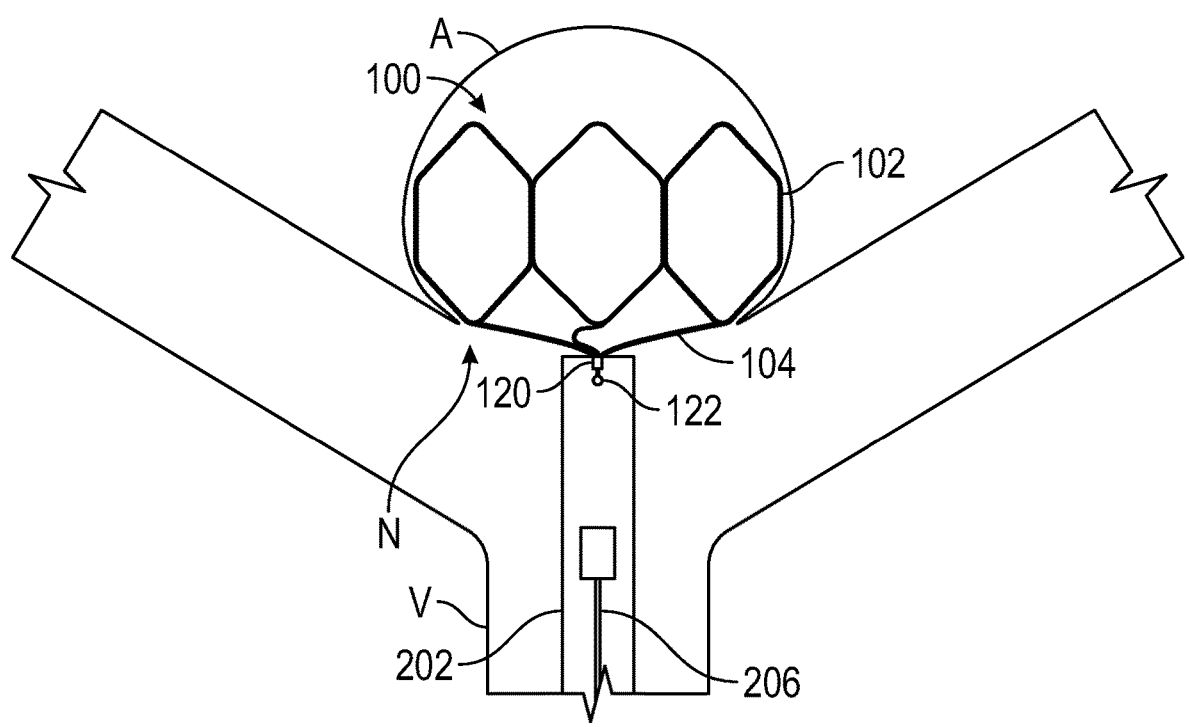
FIG. 2C is a partially schematic side view of the occlusive device of FIG. 2B after detachment from a pusher member.

Referring next to FIG. 2C, once the device 100 is deployed, the detachment element 122 and/or hub 120 can be detached from the pusher member 206. The pusher member 206 and first elongate shaft 202 can then be withdrawn from the aneurysm A.

Figure 2D:
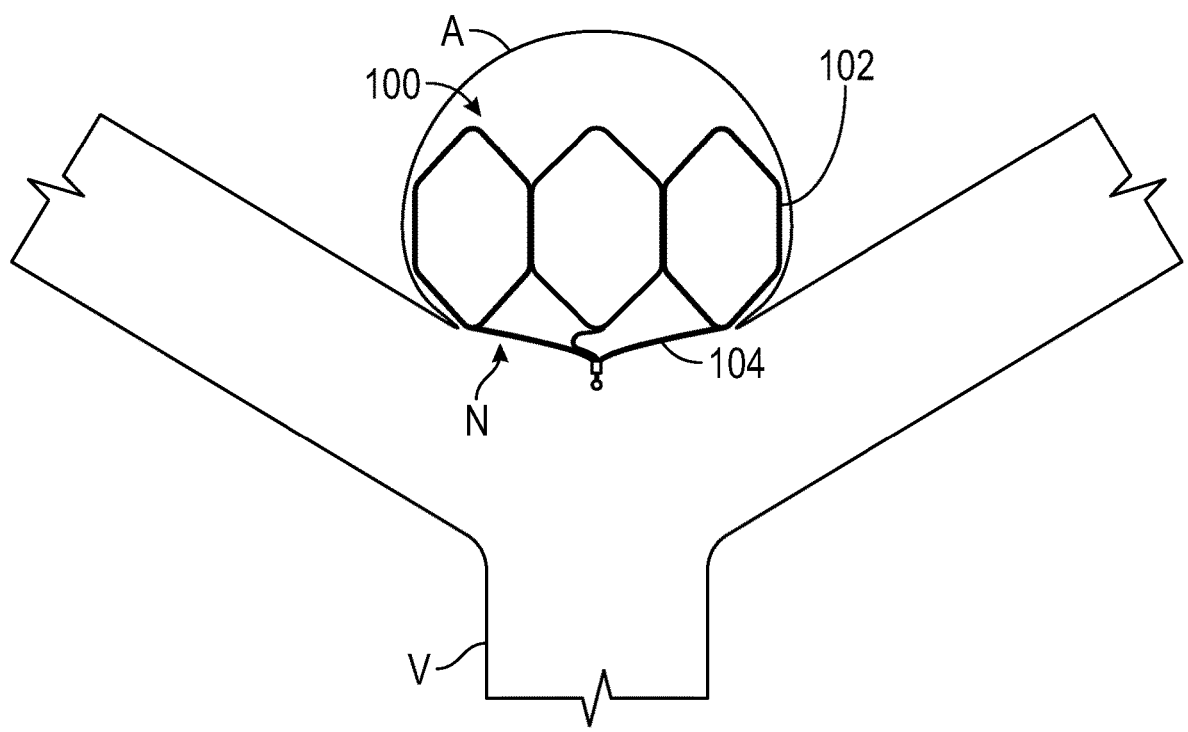
FIG. 2D is a partially schematic side view of the occlusive device of FIG. 2C after deployment.
Figure 2E:
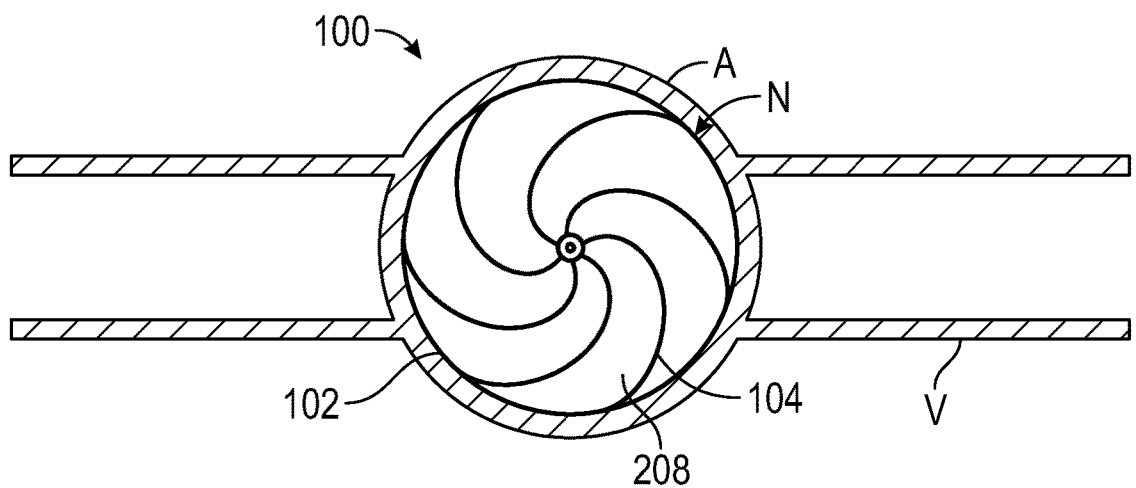
FIG. 2E is a partially schematic bottom view of the occlusive device of FIG. 2D.

Referring next to FIG. 2D, when the device 100 is deployed, the curved struts 104 are arranged in a spiral and/or helical configuration bridging the aneurysm neck N, while the tubular structure 102 engages the inner wall of the aneurysm A at or near the neck N. The tubular structure 102 and curved struts 104 can collectively generate a bracing force directly radially outward against the aneurysm wall that prevents the device 100 from being displaced out of the aneurysm A and into the vessel V. As previously described, when in the expanded configuration, the curved struts 104 can lie substantially within a single plane (e.g., the plane of the aneurysm neck N), such that there is little or no protrusion of the curved struts 104 into the vessel V. For example, when expanded, the distance between the most proximal portion of the curved struts 104 and the most proximal portion of the tubular structure 102 can be smaller than the initial distance in the low-profile configuration, such as no more than 1 mm, 0.5 mm, 0.25 mm, or 0.1 mm. This approach can be advantageous for reducing disruptions to blood flow in the vessel V, which may lead to thrombus formation. As best seen in FIG. 2E (showing a bottom view of FIG. 2D), the curved struts 104 can only partially occlude the aneurysm neck N, thus leaving one or more gaps 208 providing a passageway from the vessel V into the aneurysm A.

Figure 2F:
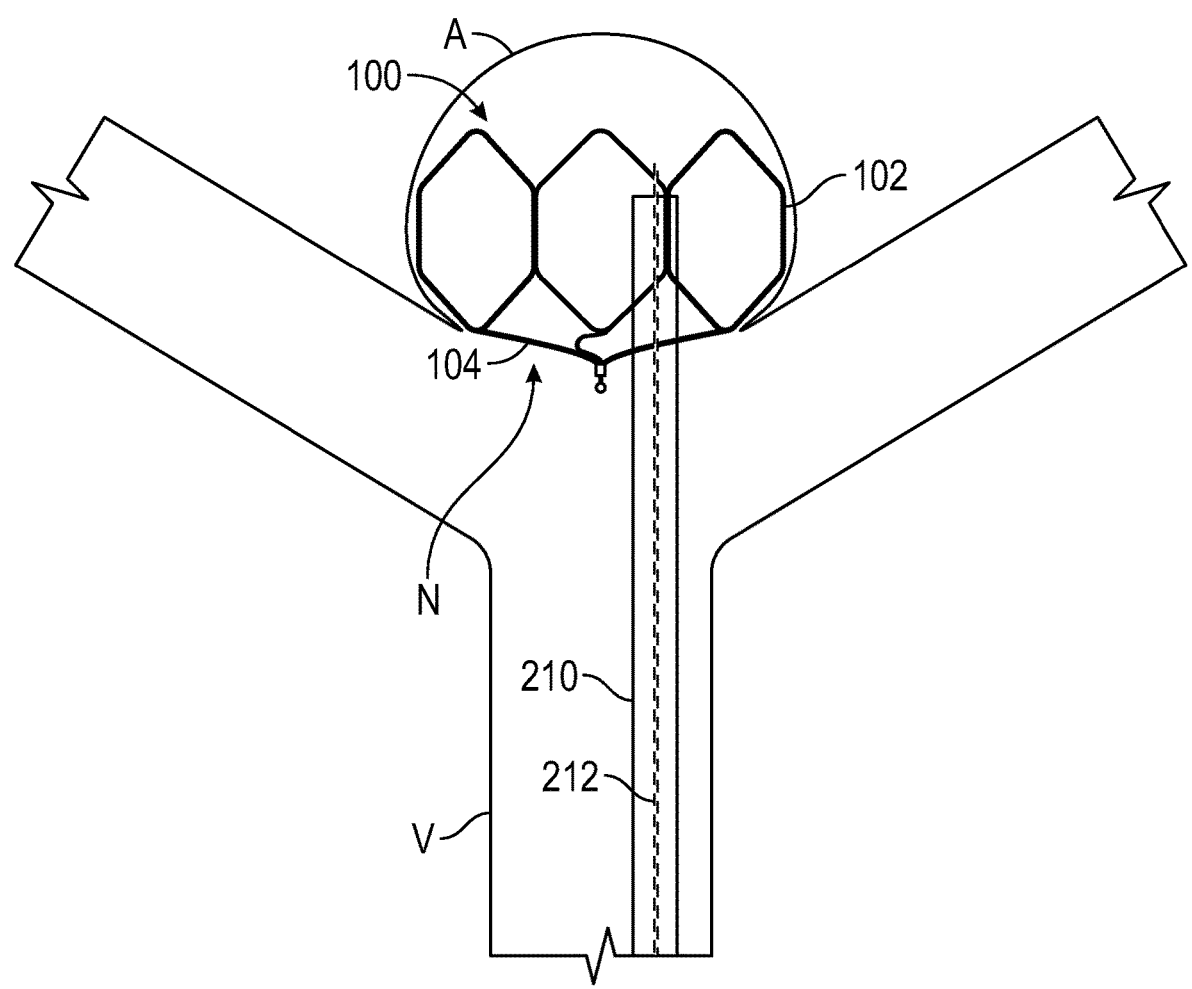
FIG. 2F is a partially schematic side view of an embolization coil being introduced into the aneurysm, together with the occlusive device of FIG. 2D.

Referring next to FIG. 2F, a second elongate shaft 210 (e.g., a second delivery catheter, such as a microcatheter) can subsequently be used to introduce an embolization coil 212, or a plurality of embolization coils, or other embolization element into the aneurysm A. The second elongate shaft 210 can be advanced through one of the gaps 208 (FIG. 2E) between the curved struts 104 and into the interior of the aneurysm A. The coil 212 can then be deployed out of the distal opening of the second elongate shaft 210 and into the aneurysm A. In other embodiments, however, the first elongate shaft 202 can be used to introduce both the device 100 and the coil 212 into the aneurysm A.

Figure 2G:
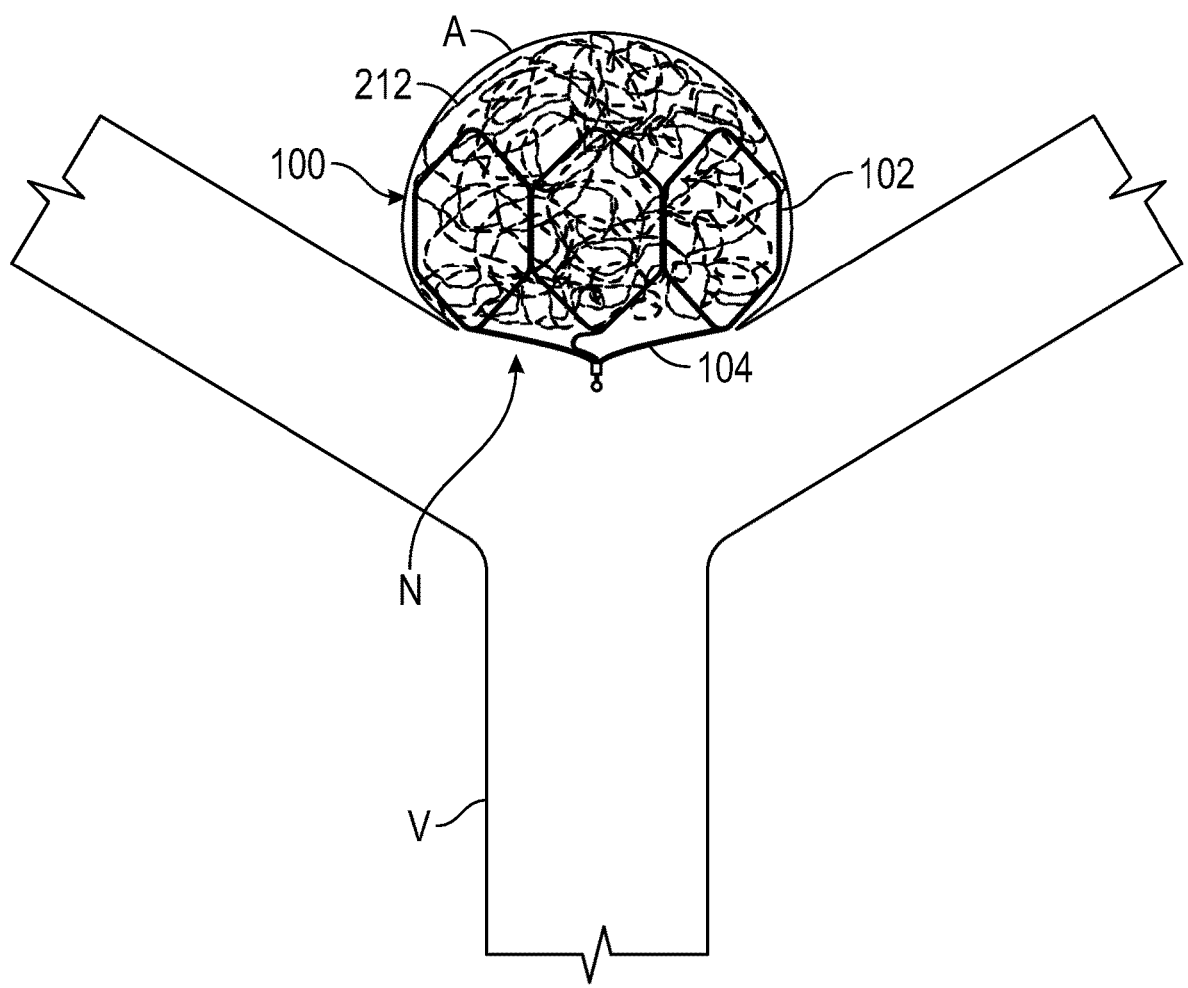
FIG. 2G is a partially schematic side view of the occlusive device and the embolization coil of FIG. 2F after deployment.

Referring next to FIG. 2G, once fully deployed, the coil(s) 212 can fill most or substantially all of the space within the aneurysm A. The coil 212 can be formed of one or more wires wound in a helical fashion about an axis to form an elongate tubular member. The wire(s) forming the coil 212 can be circular, square, or rectangular in cross-section, and can have a cross-sectional dimension (e.g., width, radius) from 0.001 inches to 0.003 inches, or from 0.0015 inches to 0.0025 inches. In some embodiments, the wire(s) forming the coil 212 have a cross-sectional dimension no greater than 0.003 inches, 0.0025 inches, or 0.002 inches. The coil 212 can be circular, square, or rectangular in cross-section, and can have a cross-sectional dimension (e.g., width, radius) from 0.01 inches to 0.02 inches, from 0.012 inches to 0.018 inches, or from 0.014 inches to 0.016 inches. In some embodiments, the coil 212 has a cross-sectional dimension that is no greater than 0.0145 inches or 0.0140 inches.

The coil 212 can have a length from 2 cm to 30 cm, from 3 cm to 25 cm, or from 4 cm to 20 cm. In some embodiments, the length of the coil 212 depends on the size of the aneurysm being treated. For example: for an aneurysm 4 mm in diameter or less, the coil 212 can have a length of about 6 cm; for an aneurysm 5 mm in diameter or less, the coil 212 can have a length of about 8 cm; for an aneurysm 6 mm in diameter or less, the coil 212 can have a length of about 15 cm; for an aneurysm 7 mm in diameter or less, the coil 212 can have a length of about 15 cm; for an aneurysm 8 mm in diameter or less, the coil 212 can have a length of about 20 cm; and, for an aneurysm 9 mm in diameter or less, the coil 212 can have a length of about 20 cm.

The coil 212 can be made from metals, alloys, polymers, shape memory materials (e.g., Nitinol), platinum, rhodium, palladium, tungsten, gold, silver, cobalt-chromium, platinum tungsten, and/or various alloys of these materials. In some embodiments, the coil 212 is heat set to form a tertiary structure (e.g., a pre-determined three-dimensional structure) when in a deployed state. For example, the coil 212 can have a preset tertiary structure that biases the coil into a bundled or more globular state that facilitates positioning of the coil 212 between the deployed device 100 and the aneurysm wall. In other embodiments, however, the coil 212 may not have a tertiary structure.

As previously mentioned, embolic coils such as the coil 212 can be very effective at filling space within the aneurysm cavity. However, there is a risk that the coil 212 may prolapse through the neck N of the aneurysm A into the vessel V, particularly if the aneurysm A is a wide-necked aneurysm. The device 100 can address this challenge via the curved struts 104 that are positioned over the aneurysm neck N to support the coil 212 and prevent the coil 212 from protruding into the neck, while the tubular structure 102 braces against the aneurysm wall to resist the outward pressure toward the vessel V exerted by the packed coil 212 so the device 100 does not bulge into the vessel V.

The methods of the present technology can be performed under fluoroscopy such that the radiopaque portions of the device 100 can be visualized by the physician to ensure proper neck coverage. If the device 100 is not positioned properly, the physician can withdraw the device 100 into the first elongate shaft 202, reposition, and deploy again. Additionally, in embodiments where the coil 212 is radiopaque, the physician can use fluoroscopy to confirm that the coil 212 does not protrude from the neck N of the aneurysm A after deployment.

FIGS. 3A-4B illustrate additional examples of occlusive devices 300, 400 for treating an aneurysm, in accordance with embodiments of the present technology. The devices 300, 400 of FIGS. 3A-4B can be generally similar to the device 100 of FIGS. 1A and 1B. Accordingly, like numbers (e.g., curved strut 104 versus curved strut 304) are used to identify similar or identical structures, and discussion of the devices 300, 400 of FIGS. 3A-4B will be limited to those features that differ from the device 100 of FIGS. 1A and 1B. Additionally, any of the features of the devices 100, 300, and 400 can be combined with each other.

Figure 3A:
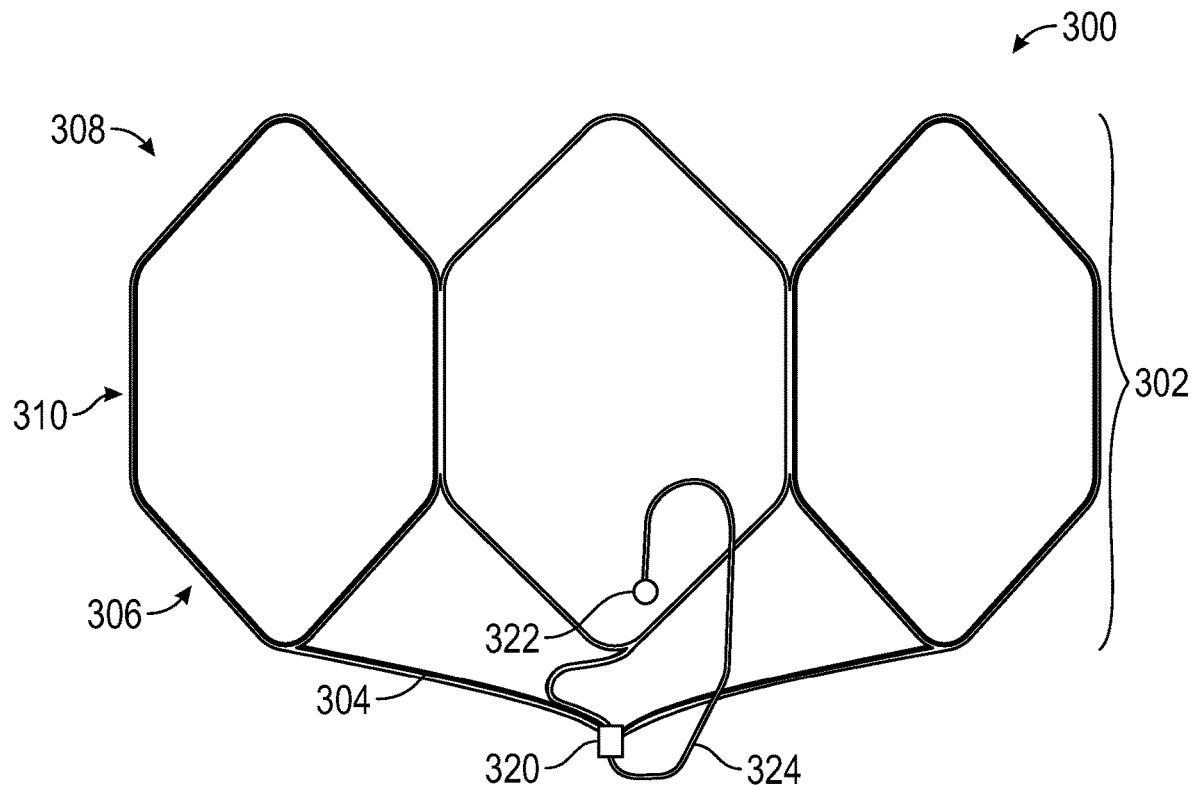
FIG. 3A is a side view of an occlusive device with a connector in an expanded configuration, in accordance with embodiments of the present technology.

Referring to FIG. 3A, the device 300 is generally similar to the device 100 of FIGS. 1A and 1B, except that the device 300 includes a connector 324 (e.g., a filament, wire, shaft, strut, or other elongate member) coupling the hub 320 to the detachment element 322. The connector 324 can have any suitable length, such as a length of at least 1 mm, 2 mm, 3 mm, 4 mm, 5 mm, 10 mm, or more. The connector 324 can be made of a flexible material having shape memory and/or superelastic properties (e.g., Nitinol), such that the connector 324 can be shape set to transform from a first (e.g., constrained) state for delivery to a second (e.g., unconstrained) state for deployment in an aneurysm.

Figure 3B:
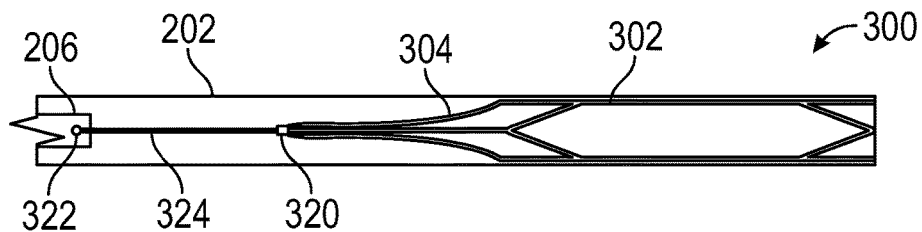
FIG. 3B is a side view of the occlusive device of FIG. 3A in a low-profile configuration.

FIG. 3B illustrates the device 300 in a low-profile configuration within the first elongate shaft 202. In the illustrated embodiment, when the device 300 is in the low-profile configuration, the connector 324 is in the first state and has a generally straightened shape that extends proximally away from the tubular structure 302 and curved struts 304. Accordingly, the detachment element 322 is accessible by and can be coupled to the pusher member 206.

Referring again to FIG. 3A, when the device 300 is deployed from the first elongate shaft 202 and separated from the pusher member 206 (e.g., in accordance with the techniques described above with respect to FIGS. 2A-2G), the connector 324 is no longer constrained and thus transforms to the second state. In the second state, the connector 324 can be bent and/or curved (e.g., coiled) in a distal direction such that at least a portion of the connector 324 and the detachment element 322 pass through the gaps between the curved struts 304 and are disposed within the lumen of the tubular structure 302 distal to the proximal end portion 306 of the tubular structure 302. Accordingly, when the device 300 is deployed in the aneurysm, the connector 324 and detachment element 322 can be contained partially or entirely within the aneurysm sac, thus avoiding disruptions to blood flow in the parent vessel.

Figure 4A:
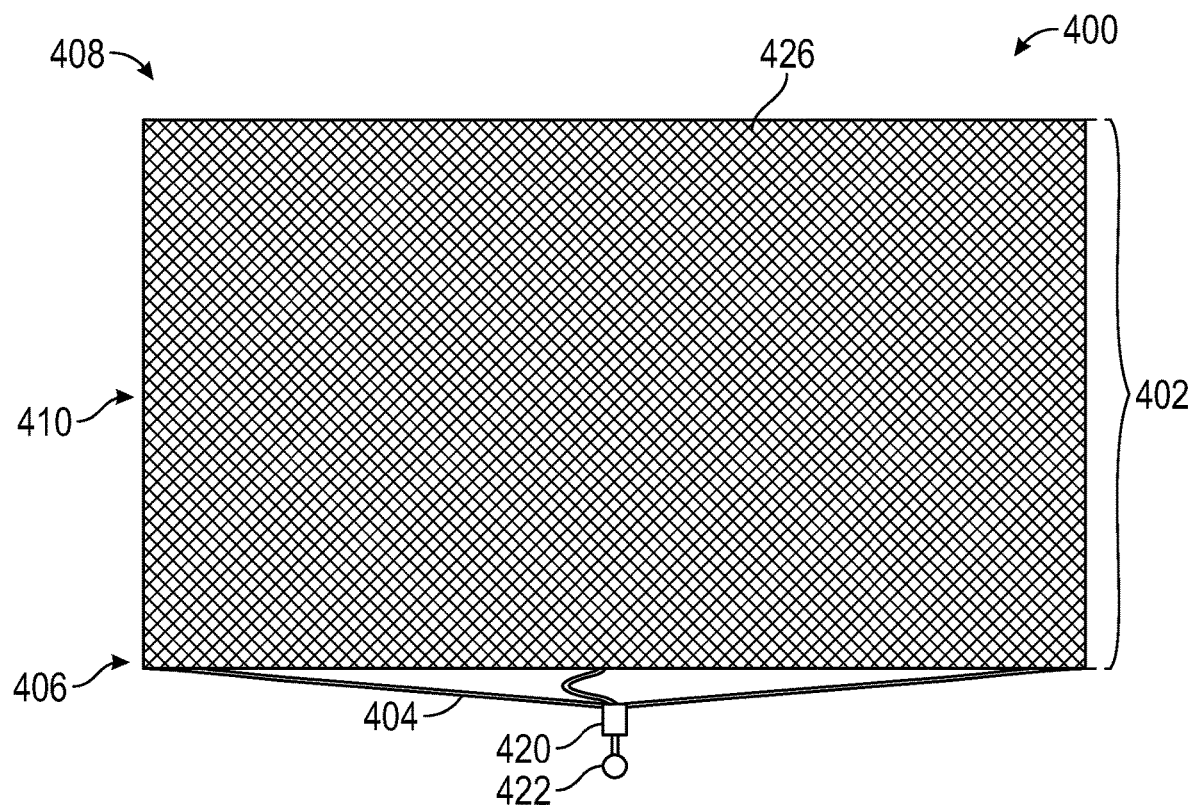
FIG. 4A is a side view of an occlusive device including a braided tubular structure in an expanded configuration, in accordance with embodiments of the present technology.
Figure 4B:
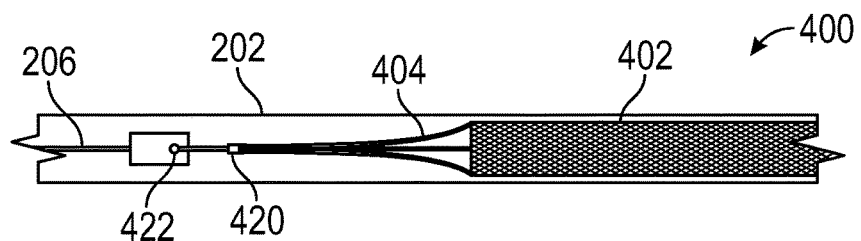
FIG. 4B is a side view of the occlusive device of FIG. 4A in a low-profile configuration.

Referring next to FIG. 4A, the device 400 is generally similar to the device 100 of FIGS. 1A and 1B, except that the tubular structure 402 is a braid formed from a plurality of filaments 426 (e.g., wires). The filaments 426 are braided, woven, or otherwise interconnected to form the mesh surface 410 of the tubular structure 402. The braid can be self-expandable such that the device 400 can transform from a low-profile configuration (FIG. 4B) in which the braid is radially constrained and/or compressed, to an expanded configuration (FIG. 4A) in which the braid is expanded radially outward to engage the aneurysm wall.

In some embodiments, some or all of the filaments 426 (e.g., at least 25%, 50%, 80%, or 100% of the filaments 426) are made of one or more shape memory and/or superelastic materials (e.g., Nitinol). The braid can have, for example, from 32 to 144 filaments 426, such as 64 or 72 filaments 426. Some or all of the filaments 426 can have a diameter from 0.0010 inches to 0.0012 inches, such as a diameter of 0.0010 inches, 0.0011 inches, or 0.0012 inches (at least prior to etching). In some embodiments, some or all of the filaments 426 are drawn-filled tubes ("DFT") having a radiopaque core (e.g., platinum) surrounded by a shape memory alloy and/or superelastic alloy (e.g., Nitinol, cobalt chromium, etc.). Radiopaque markers can alternatively or additionally be incorporated into other portions of the device 400, e.g., at or near the distal end portion 408, proximal end portion 406, curved struts 404, hub 420, etc. All or a portion of the length of some or all of the filaments 426 can have one or more coatings or surface treatments. For example, some or all of the filaments 426 can have a lubricious coating or treatment that reduces the delivery force as the device 400 is advanced through the delivery catheter. In some embodiments, the coating is relatively hydrophilic, such as a phosphorocholine compound. Additionally or alternatively, some or all of the filaments 426 can have a coating or treatment (the same as the lubricious coating, or a different coating) that enhances blood compatibility and reduces the thrombogenic surface activity of the braid. Optionally, at least a portion of the filaments 426 can be made of other suitable materials.

In some embodiments, the tubular structure 402 and curved struts 404 are integrally formed as a single unitary component. For example, the curved struts 404 can be formed from the same filaments 426 used to form the braid of the tubular structure 402. In such embodiments, each curved strut 404 can be made from one or more filaments 426 that are bundled, twisted, braided, or otherwise assembled into a single elongate component. Alternatively, the tubular structure 402 and curved struts 404 can be discrete components that are attached to each other, e.g., using welding, adhesives, fasteners, or other suitable techniques. In such embodiments, the curved struts 404 can be formed of known flexible materials, including shape memory and/or superelastic materials (e.g., Nitinol), cobalt chromium, platinum, stainless steel, other metals or metal alloys, or a combination thereof, and can be manufactured by laser-cutting, etching, metal injection molding, braiding, etc.

CONCLUSION

Although many of the embodiments are described above with respect to systems, devices, and methods for treating a cerebral aneurysm, the technology is applicable to other applications and/or other approaches. For example, the occlusive devices, systems, and methods of the present technology can be used to treat any vascular defect and/or fill or partially fill any body cavity or lumen or walls thereof, such as for parent vessel take down, endovascular aneurysms outside of the brain, arterial-venous malformations, embolization, atrial and ventricular septal defects, patent ductus arteriosus, and patent foramen ovale. Additionally, several other embodiments of the technology can have different states, components, or procedures than those described herein. It will be appreciated that specific elements, substructures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above with reference to FIGS. 1A-4B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A system for treating an aneurysm, the system comprising:
   an embolization coil; and
   an occlusive device comprising:
   a tubular structure having a first end portion with a first opening, a second end portion with a second opening, and a mesh surface extending between the first and second end portions; and
   a plurality of spiral struts coupled to the first end portion of the tubular structure and extending across the first opening and defining a plurality of spiral openings between adjacent spiral struts of the plurality of spiral struts, wherein, when the occlusive device is deployed within the aneurysm, the tubular structure and the plurality of spiral struts are configured to self-expand such that the plurality of spiral struts span a neck of the aneurysm substantially within a single plane, the mesh surface of the tubular structure engages a wall of the aneurysm near the neck, and the second end portion with the second opening is positioned within the aneurysm distal to the plurality of spiral struts, and the occlusive device is configured to partially occlude the neck of the aneurysm, and wherein the plurality of spiral struts are configured for the embolization coil to be inserted through one of the spiral openings into an interior volume of the tubular structure and to retain the embolization coil within the aneurysm, and the second opening is configured to receive the embolization coil such that the embolization coil is retained at least partially within the interior volume of the tubular structure.

2. The system of claim 1, wherein the tubular structure comprises a stent including a plurality of cells.

3. The system of claim 1, wherein the tubular structure comprises a braid formed from a plurality of filaments.

4. The system of claim 1, wherein the plurality of spiral struts are arranged in a radial configuration.

5. The system of claim 1, further comprising a hub, wherein each spiral strut includes a first end region coupled to the hub, and a second end region coupled to the first end portion of the tubular structure.

6. The system of claim 5, wherein the second end region of each spiral strut is coupled to a peripheral edge of the tubular structure.

7. The system of claim 1, further comprising a detachment element configured to releasably couple the tubular structure and the plurality of spiral struts to a pusher member.

8. The system of claim 7, further comprising a hub, wherein the detachment element is coupled to the plurality of spiral struts via the hub.

9. The system of claim 8, further comprising an elongate member connecting the detachment element to the hub, wherein the elongate member is configured to transform from a first state to a second state when the occlusive device is deployed within the aneurysm.

10. The system of claim 9, wherein:
when in the first state, the elongate member extends away from the tubular structure, and
when in the second state, the elongate member is positioned at least partially within the tubular structure.

11. The system of claim 1, wherein, when the occlusive device is deployed within the aneurysm, the plurality of spiral struts are contained entirely within the aneurysm.

12. The system of claim 1, wherein the embolization coil is configured to fill a space within the aneurysm.

13. The occlusive devicesystem of claim 1, wherein the embolization coil comprises one or more wires biased to form a pre-determined structure.

14. The system of claim 1, wherein the embolization coil is configured to disrupt blood flow into the aneurysm when the embolization coil is retained at least partially within the interior volume of the tubular structure.

15. A system for treating an aneurysm, the system comprising:

an embolization coil configured to be positioned within the aneurysm; and
an occlusive device comprising:
a tubular structure having a first end portion with a first opening, a second end portion with a second opening, and a mesh surface extending between the first and second end portions; and
a plurality of spiral struts coupled to the first end portion of the tubular structure and extending over the first opening, wherein the plurality of spiral struts define one or more gaps therebetween,
wherein, when the occlusive device is deployed within the aneurysm, the tubular structure and the plurality of spiral struts are configured to self-expand such that the plurality of spiral struts span a neck of the aneurysm substantially within a single plane with the one or more gaps providing at least one passageway into the aneurysm, and the mesh surface of the tubular structure engages a wall of the aneurysm near the neck, and
wherein the plurality of spiral struts are configured to retain the embolization coil within the aneurysm.

16. The system of claim 15, wherein the tubular structure comprises a stent including a plurality of cells.

17. The system of claim 15, wherein the tubular structure comprises a braid formed from a plurality of filaments.

18. The system of claim 15, wherein the plurality of spiral struts are arranged in a radial configuration.

19. The system of claim 15, further comprising a hub, wherein each spiral strut includes a first end region coupled to the hub, and a second end region coupled to the first end portion of the tubular structure.

20. The system of claim 19, wherein the second end region of each spiral strut is coupled to a peripheral edge of the tubular structure.

21. The system of claim 15, further comprising a detachment element configured to releasably couple the tubular structure and the plurality of spiral struts to a pusher member.

22. The system of claim 21, further comprising a hub, wherein the detachment element is coupled to the plurality of spiral struts via the hub.

23. The system of claim 22, further comprising an elongate member connecting the detachment element to the hub, wherein the elongate member is configured to transform from a first state to a second state when the occlusive device is deployed within the aneurysm.

24. The system of claim 23, wherein:
when in the first state, the elongate member extends away from the tubular structure, and
when in the second state, the elongate member is positioned at least partially within the tubular structure.

25. The system of claim 15, wherein, when the occlusive device is deployed within the aneurysm, the plurality of spiral struts are contained entirely within the aneurysm.

26. The system of claim 15, wherein the at least one passageway is configured to allow insertion of the embolization coil into the aneurysm.

27. The system of claim 15, wherein the plurality of spiral struts define a plurality of gaps therebetween, such that when the occlusive device is deployed within the aneurysm, the occlusive device partially occludes the neck of the aneurysm.

* * * * *